United States Patent

Grundei

[11] Patent Number: 5,458,644
[45] Date of Patent: Oct. 17, 1995

[54] KNEE JOINT ENDOPROSTHESIS

[75] Inventor: Hans Grundei, Luebeck, Germany

[73] Assignee: Eska Medical GmbH & Co., Luebeck, Germany

[21] Appl. No.: 990,955

[22] Filed: Dec. 15, 1992

[30] Foreign Application Priority Data

Dec. 18, 1991 [DE] Germany ............ 41 41 757.7

[51] Int. Cl.⁶ ..................................... A61F 2/38
[52] U.S. Cl. ........................................... 623/20
[58] Field of Search ................. 623/16, 18, 19, 623/20

[56] References Cited

U.S. PATENT DOCUMENTS

| 3,765,033 | 10/1973 | Goldberg et al. | 623/20 |
|---|---|---|---|
| 3,837,009 | 9/1974 | Walker | 623/20 |
| 3,885,252 | 5/1975 | Nakajima | 623/20 |
| 3,996,624 | 12/1976 | Noiles | 623/20 |
| 4,064,568 | 12/1977 | Grundei et al. | 623/20 |
| 4,112,522 | 9/1978 | Dadurian et al. | 623/20 |
| 4,216,549 | 8/1980 | Hillberry et al. | 623/20 |
| 4,358,859 | 11/1982 | Schurman et al. | 3/1.911 |
| 4,462,120 | 7/1984 | Rambert et al. | 623/20 |
| 5,123,928 | 6/1992 | Moser | 623/20 |
| 5,147,405 | 9/1992 | Van Zile et al. | 623/20 |
| 5,181,925 | 1/1993 | Houston et al. | 623/20 |

FOREIGN PATENT DOCUMENTS

| 0178445 | 4/1986 | European Pat. Off. | 623/20 |
|---|---|---|---|
| 2245327 | 4/1975 | France . | |
| 2330375 | 6/1977 | France . | |
| 2566657 | 1/1986 | France . | |
| 2628316 | 9/1989 | France . | |
| 2607316 | 9/1976 | Germany . | |
| 2452412 | 3/1982 | Germany | 623/20 |
| 3343606 | 7/1985 | Germany | 623/20 |

OTHER PUBLICATIONS

Copy of European Search Report concerning EP 92 12 0890, Mar. 3, 1993.

Primary Examiner—David Isabella
Attorney, Agent, or Firm—Panitch Schwarze Jacobs & Nadel

[57] ABSTRACT

A knee joint endoprosthesis includes a shaft piece (1) which is anchored in the femur bone and a connected femur component (2) with two gliding runners (3, 4), which are anteriorly connected by a bridge (6) carrying a connecting element (5) to the shaft piece (1) and defining between the runners a groove (7) extending anteriorly to posteriorly. This groove is bordered on both sides, in the femur direction, by struts (8, 8') which have channels (9, 9') with a partially circular cross section running laterally from the groove and aligned with each other. The tibia component (10) has two gliding surfaces (11, 12), on which the gliding runners (3, 4) of the femur component (2) perform a gliding movement, a strut (13) which is directed toward the femur between the two gliding surfaces (11, 12) and reaches through the groove (7) of the femur component (2) and rides tightly against its inner surfaces. The tibia component (10) has in the upper region of the strut (13) a cylindrical guide bolt (14, 15) extending laterally from the center, which lies in the channels (9, 9') of the struts (8, 8') of the femur component (2) and is secured in position by enclosing parts (17) of the shaft piece (1). The endoprosthesis has more stability than conventional hinged prostheses.

10 Claims, 3 Drawing Sheets

KNEE JOINT ENDOPROSTHESIS

FIELD OF THE INVENTION

The invention concerns a knee joint endoprosthesis, having a femur component anchored in the femur bone and a tibia component anchored in the tibia bone, the femur component having gliding runners which bear on gliding surfaces of the tibia component.

BACKGROUND OF THE INVENTION

A number of artificial knee joints are known which are implanted as substitutes for the natural knee joints in the human body.

These endoprosthesis can be divided into two general groups. The joints of the one group make use of a relatively intact band or belt device and attempt, based on their construction, to permit as far as possible a physiological mode of movement. An example of such a knee joint endoprosthesis is shown in German Patent No. DE 39 22 294 (U.S. Pat. No. 5,123,928).

There are also known hinge type endoprostheses in which the femoral and the tibia parts of the prosthesis are connected with each other by a hinge joint. There is no need for a band device with these joints. They are most commonly used for heavily damaged joints, where it is consequently not so important to achieve a highly physiological mode of movement, but mainly just to make an implantation of an artificial joint possible.

The main problem with known hinged endoprostheses is stability. The hinge itself of the conventional joint endoprosthesis must bear all the resulting stresses, which occur during walking, from the tibia into the femur bone and vice versa. Also during load changes the hinge is stressed. In practice, this leads to problems of stability, namely to the tendency that the hinge pops out.

The purpose of the present invention is to develop a knee joint endoprosthesis for heavily damaged joints, which is strong enough to resist over an extended period of time all occurring stress, including load changes.

SUMMARY OF THE INVENTION

This purpose is achieved by the knee joint endoprosthesis according to the present invention with the features described and claimed below. The knee joint endoprosthesis according to the invention comprises a shaft piece which is anchored in the femur bone and a femur component connected thereto, the femur component having two gliding runners which are anteriorly connected together by a bridge which carries a connecting element to the shaft piece. The runners define between them a groove running ventral (front) to dorsal (back). The groove is bordered on each side, in the direction of the femur, by a strut, each strut having a channel with a partially circular cross section running laterally from the middle. The two channels are aligned with each other.

There is also a tibia component which has two gliding planes or surfaces, on which the gliding runners of the femur component can perform a gliding movement, a strut between the two gliding surfaces which is directed toward the femur and which reaches through the groove of the femur component and rides tightly on its inner surfaces. In the upper region of the strut a cylindrical guide bolt extends laterally from the center. This guide bolt lies in the channels of the struts in the femur component. It is secured in this position by an enclosing part of the femur shaft piece.

The force transmission in the knee joint endoprosthesis of the invention takes place—except during load shifts—directly through the gliding surfaces of the tibia component and the gliding runners of the femur component. Load changes are absorbed by the inner sides of the groove in the femur component, as well as by the strut of the tibia component which reaches through the groove and rides tightly against the femur component. Hence, the guide bolt merely has a guiding function, in order to bend the femur component, i.e., as an axis of rotation, in relation to the tibia component. This is the main advantage compared to conventional hinge prostheses.

As with those, each point of the femoral gliding runners makes a circular motion around the axis of rotation, formed by the guide bolt, during bending of the joint. Hence, the locus of each point of the gliding runners is a circular path.

On account of the transfer of the load transmission function to the gliding planes on the one hand, and to the strut of the tibia component on the other hand, an excellent long term stability is achieved.

The enclosing parts of the shaft piece are necessary in order to hold the guide bolt in the channels of the femur component. The parts can be complementary formed plates of the shaft piece. The connection of the femur component to the shaft piece can occur in known manner through a conical interference or friction fit between a cone-shaped connecting element of the femur component on the one hand and a cone-shaped sleeve in the shaft piece on the other hand.

The femur component is preferably made of metal, whereas the contacting pieces of the tibia component, namely the gliding surfaces, the struts and the guide bolt, have outer surfaces of wear-resistant plastic.

The strut of the tibia component is preferably reinforced by a metal core in order to securely withstand the resulting stresses during load shifts without yielding. The guide bolt can also be reinforced with an inner metal core to ensure operation of its guiding function over a long period of time.

The upper surfaces of the gliding planes of the tibia component and the outer surfaces of the strut are preferably unitary and formed from a single piece which is connected with the otherwise metallic tibia component. This permits, should there be an eventual need for corrective surgery after excessive wear of the plastic, a relatively simple substitution of the gliding partners for the femoral gliding runners.

Advantageously, the metallic core of the strut is constructed of one piece with the other metallic parts of the tibia component. By this means problems that could occur from a connection between the metal core and the tibia component are avoided.

So that the guide bolt performs its guiding function as optimally as possible, the channels in the femur component preferably having a depth which corresponds essentially to half the diameter of the guide bolt.

Another advantage of the endoprosthesis of the invention arises because it is composed from modular components and nevertheless guarantees an excellent stability. On account of its construction, it is possible to assemble the endoprosthesis without any screw connections, which could loosen over a period of time.

BRIEF DESCRIPTION OF THE DRAWINGS

The foregoing summary of the invention, as well as the following detailed description of the preferred embodiment, will be better understood when read in conjunction with the appended drawings. For the purpose of illustrating the invention, there is shown in the drawings an embodiment which is presently preferred, it being understood, however, that the invention is not limited to the specific arrangement and instrumentalities disclosed.

In the Figures, like components are designated with the same reference numerals.

DETAILED DESCRIPTION OF THE PREFERRED EMBODIMENT

Figure 1:
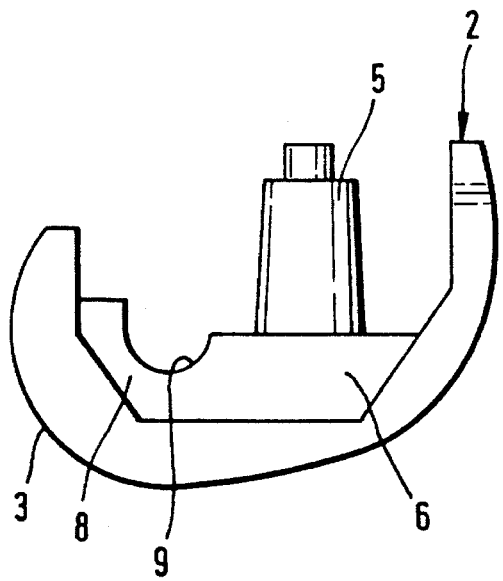
FIG. 1 is a side view of the femur component.
Figure 2:
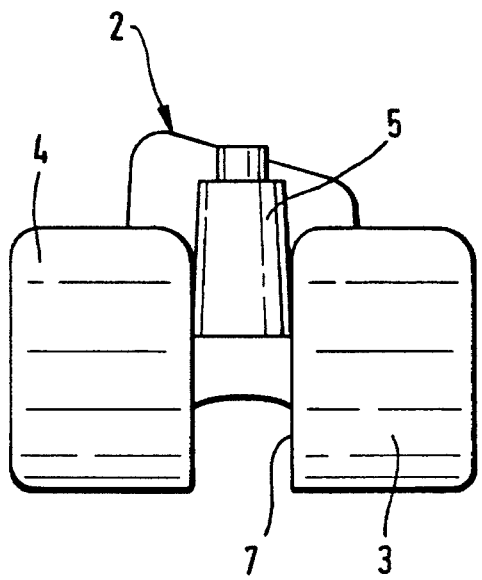
FIG. 2 is a dorsal view of the femur component.
Figure 3:
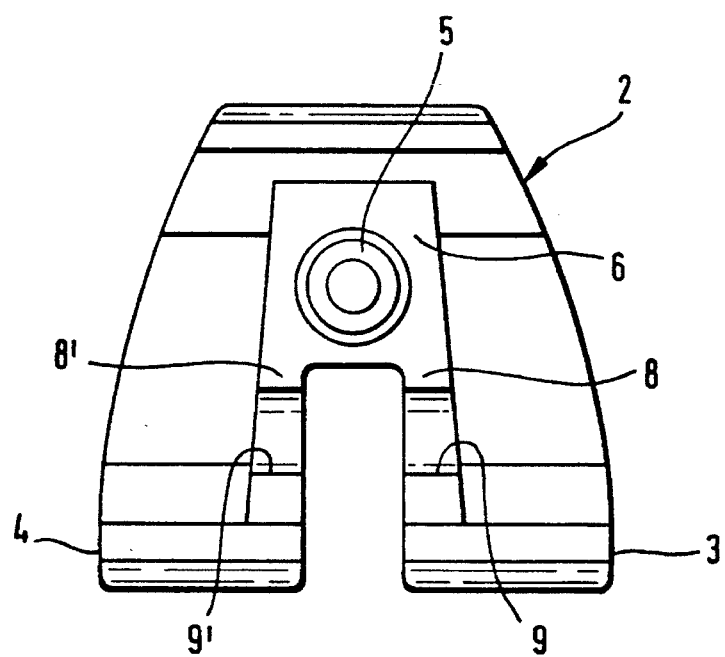
FIG. 3 is a top view of the femur component.
Figure 6:
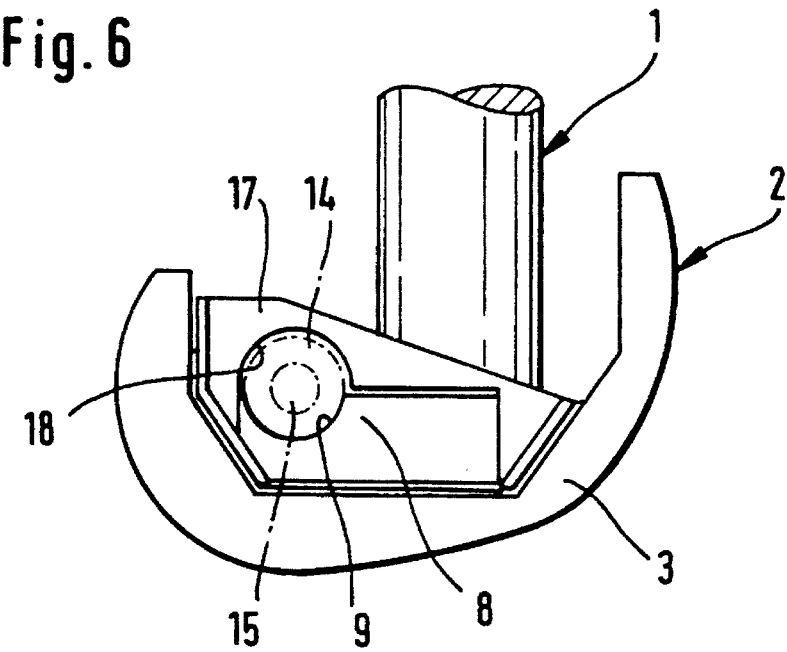
FIG. 6 is a side view of the femur component and the shaft piece of the endoprosthesis.
Figure 7:
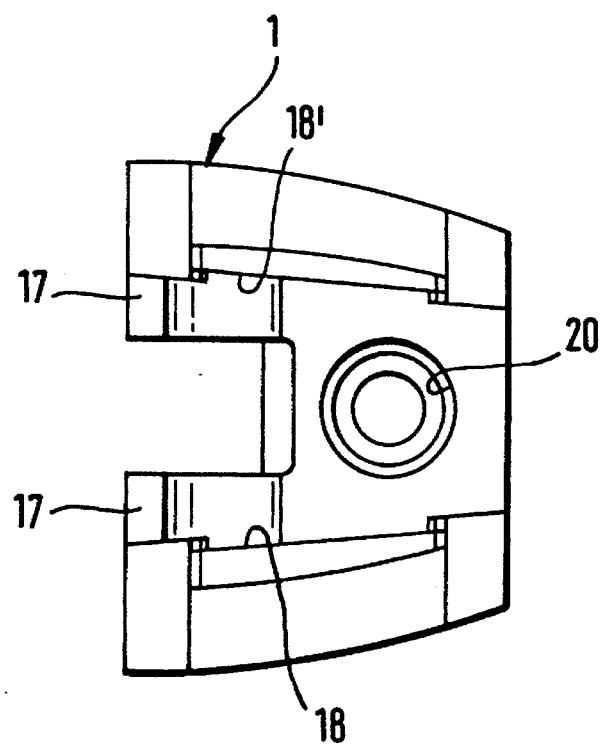
FIG. 7 is a view of the underside of the shaft piece.

FIG. 1 shows the femur component 2 which is connectable with a shaft piece anchored in the femur bone. The femur component comprises two gliding runners 3 and 4 (FIG. 2), which are anteriorly connected by a bridge 6 (FIG. 3). The bridge 6 further carries a connecting element 5 (FIG. 1), which in the present case is in the form of a conical pin. This finds its complement in a conical sleeve 20 (FIG. 7) in the shaft piece 1 (FIG. 6). Between this conical sleeve 20 and the connecting element 5 a connection is created in known manner by conical interference fit. The two gliding runners 3 and 4 of the femur component 2 define between them a groove 7 (FIG. 2) running from front to back. This groove 7 is bordered on both sides toward the femur by struts 8, 8' (FIG. 3). In each of the two struts 8, 8', there is provided a channel 9, 9', running laterally from the middle with a partially circular cross section (FIG. 1). The two channels 9, 9' are aligned with each other (FIG. 3).

Figure 4:
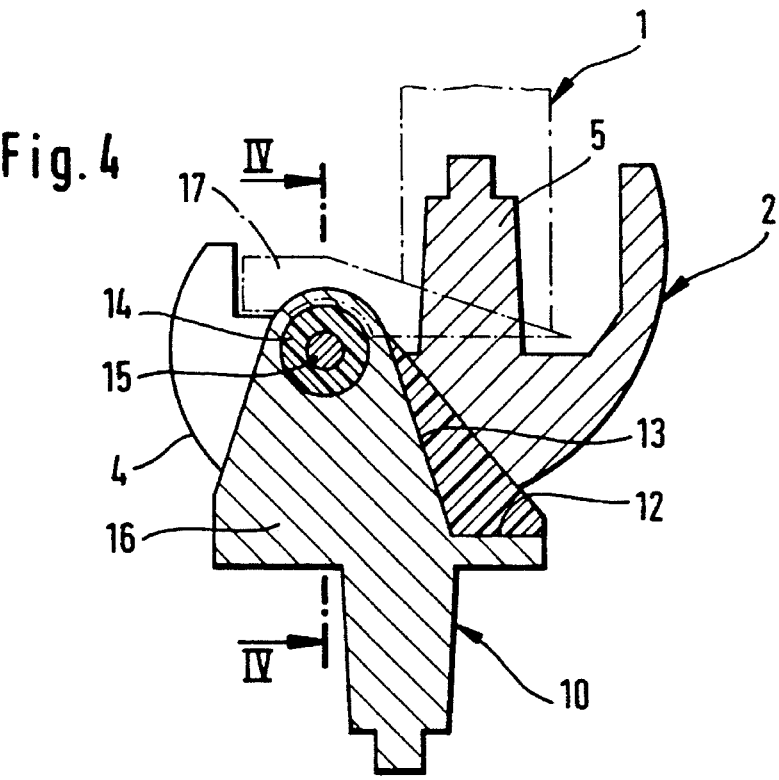
FIG. 4 is a cross-sectional view of the endoprosthesis in the plane of the strut of the tibia component.
Figure 5:
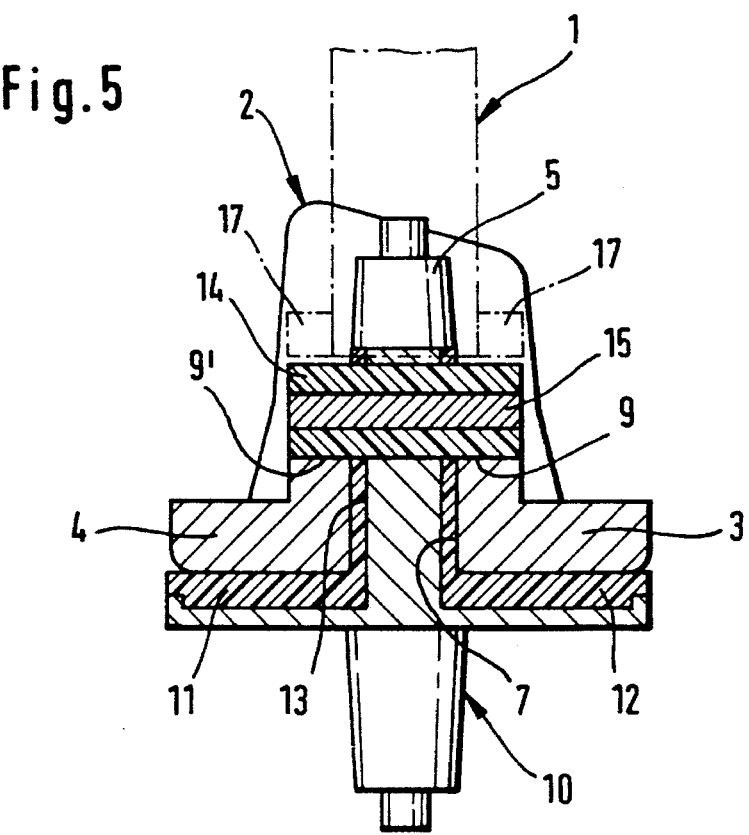
FIG. 5 is a cross-sectional view along line IV—IV of FIG. 4.

The cooperation of the femur component 2 with the tibia component 10 is clarified in FIGS. 4 and 5. The tibia component 10 has two gliding surfaces 11, 12, on which the gliding runners 3, 4 of the femur component perform their gliding motion (FIG. 5). The tibia component 10 has between the two gliding surfaces 11 and 12 a strut 13 which extends in the direction of the femur and which reaches through the groove 7 of the femur component and rides tightly on its inner surfaces (FIG. 5). Through the tight arrangement of the strut 13 against the inner surfaces of the groove 7, the forces arising during a load change are conducted from the femur component 2 to the tibia component 10 with little play.

The tibia component 10 also has a cylindrical guide bolt 14,15 which runs laterally from the center in the upper region of the strut 13 (FIGS. 4 and 5) and which lies in the channels 9, 9' of the struts 8, 8' in the femur component 2. The guide bolt 14, 15 forms in its bearing in channels 9 and 9' the axis of rotation or bending of the joint. The guide bolt is secured in position by the enclosing parts 17 of the shaft piece 1 (FIG. 6). In the embodiment shown the parts 17 are formed by a complementary surface shape with corresponding cutouts 18 and 18' (FIG. 7), in such a way that the guide bolt 14, 15 is practically surrounded in the manner of a pipe by the channels 9 and 9', as well as by the cutouts 18 and 18' in the parts 17 of the shaft piece 1. As can be seen in FIG. 6 the channels 9 and 9' closely conform to the guide bolt 14, 15 on the bottom and sides, and the cutouts 18 and 18' hold the bolt in these channels from the top, so that only one degree of freedom of movement is allowed for the prosthesis, namely rotation (flexing) about the bolt in the manner of a hinge. As already stated, the connection of the femur component 2 to the shaft piece 1 takes place by conical interference fit.

In the embodiment shown the tibia component 10 is represented as a piece, which still needs to be connected with a shaft piece (not shown). Of course, it could also be constructed as one piece with the shaft, if desired.

As distinctly shown in FIG. 5, the parts of the tibia component 10, which are touching the femur component 2, are made of a wear resistant plastic, which can be seen by the different lining of these parts. Hence, the gliding surfaces 11 and 12, the outer surfaces of the strut 13, as well as the outer surface 14 of the guide bolt 15, are made of such a material. Furthermore, in FIG. 5 the preferred embodiment is made clear, whereby the outer surfaces of the strut 13 are constructed from such a plastic as one piece with the gliding surfaces 11 and 12 of the tibia component.

As can also be seen from FIG. 5, the strut 13 has a metal core 16, by means of which it is reinforced. This metal core is constructed in the embodiment shown as one piece with the other metallic parts of the tibia component (See also FIG. 4). Also, in the preferred embodiment, the guide bolt is reinforced by an inner metal core 15.

For reasons of illustration the femoral shaft piece 1 is only shown by dotted lines in FIGS. 4 and 5. However, it shows how the parts 17 serve for securing the position of the guide bolt 14, 15 in the channels 9, 9'.

The present invention may be embodied in other specific forms without departing from the spirit or essential attributes thereof and, accordingly, reference should be made to the appended claims, rather than to the foregoing specification as indicating the scope of the invention.

I claim:

1. A knee joint endoprosthesis comprising an elongated shaft (1) configured for anchoring in a femur bone, a femur component (2) having a connecting element (5) to provide a means for connecting said femur component (2) to said shaft (1), said femur component having two gliding runners (3, 4) which are anteriorly connected with a bridge (6) carrying connecting element (5), said runners defining a groove (7) extending anteriorly to posteriorly between runner (3) and runner (4), said groove having inner surfaces and bordered on both sides by struts (8, 8'), each of said struts each having a channel (9, 9') formed therein, said channel having a partially circular cross section running laterally from a central portion thereof, said channels (9, 9') being aligned with each other, a tibia component (10) having two gliding surfaces (11, 12), on which the gliding runners (3, 4) of the femur component (2) perform a gliding movement, a tibial strut (13) extending outwardly toward the femur component (2) between the two gliding surfaces (11, 12), said tibial strut (13) reaching through the groove (7) of the femur component (2) and bearing tightly against the inner surfaces of the groove, a cylindrical guide bolt (14, 15) extending laterally from a central portion in an upper area of the tibial strut (13), said guide bolt having a diameter configured to lie in the channels (9, 9') of the struts (8, 8') of the femur component (2) and secured in position by an enclosing part (17) of shaft (1), so as to allow only one degree of freedom for movement of the prosthesis.

2. A knee joint endoprosthesis according to claim 1 wherein the femur component (2) is made of metal and gliding surfaces (11, 12), tibial strut (13) and guide bolt (14, 15) of the tibia component (10) which contact the femur component (2) have surfaces made of wear-resistant plastic.

3. A knee joint endoprosthesis according to claim 1 wherein the tibial strut (13) is reinforced by a metal core (16).

4. A knee joint endoprosthesis according to claim 2 wherein the guide bolt is reinforced by an inner metal core (15).

5. A knee joint endoprosthesis according to claim 3 wherein the guide bolt is reinforced by an inner metal core (15).

6. A knee joint endoprosthesis according to claim 2 wherein the gliding surfaces (11, 12) and an outer surface of the tibial strut (13) comprise a unitary attachment piece, which is connected to the tibia component (10), the tibia component (10) other than said unitary attachment piece being made of metal.

7. A knee joint endoprosthesis according to claim 3 wherein the gliding surfaces (11, 12) and an outer surface of the tibial strut (13) comprise a unitary attachment piece, which is connected to the tibia component (10).

8. A knee joint endoprosthesis according to claim 4 wherein the gliding surfaces (11, 12) and an outer surface of the tibial strut (13) comprise a unitary attachment piece, which is connected to the tibia component (10), the tibia component (10) other than said unitary attachment piece being made of metal.

9. A knee joint endoprosthesis according to claim 3 wherein the metal core (16) of the tibial strut (13) is formed as one piece with parts of the tibia component (10) which are made of metal.

10. A knee joint endoprosthesis according to claim 1 wherein the channels (9, 9') have a depth, which is essentially half the diameter of guide bolt (14, 15).

* * * * *